United States Patent [19]

Gadelius

[11] Patent Number: 5,616,147
[45] Date of Patent: Apr. 1, 1997

[54] MEANS TO SAFELY DETERMINE THE MUTUAL POSITIONS OF A FEMUR AND AN ILIUM IN HIP SURGERY

[75] Inventor: Gustaf Gadelius, Stockholm, Sweden

[73] Assignee: Meduse Scandinavia AB, Stockholm, Sweden

[21] Appl. No.: 446,625

[22] PCT Filed: Nov. 26, 1993

[86] PCT No.: PCT/SE93/01020

§ 371 Date: Jun. 30, 1995

§ 102(e) Date: Jun. 30, 1995

[87] PCT Pub. No.: WO94/12109

PCT Pub. Date: Jun. 9, 1994

[30] Foreign Application Priority Data

Nov. 26, 1992 [SE] Sweden ................... 9203579

[51] Int. Cl.⁶ ............ A61B 17/58; A61B 17/60
[52] U.S. Cl. .................. 606/102; 606/96; 606/89
[58] Field of Search ................ 606/87, 90, 86, 606/89, 91, 99, 102, 105

[56] References Cited

U.S. PATENT DOCUMENTS 5,122,145  6/1992  Fishbane ................... 606/102
5,141,512  8/1992  Farmer et al. ............. 606/87
5,213,112  5/1993  Niwa ......................... 606/99
5,385,567  1/1995  Goble ....................... 606/102

FOREIGN PATENT DOCUMENTS 2684287      6/1993  France .
WO93/22981  11/1993  WIPO .

Primary Examiner—Michael Powell Buiz
Assistant Examiner—Mark S. Leonardo
Attorney, Agent, or Firm—Young & Thompson

[57] ABSTRACT

Apparatus to determine the mutual positions of a femur head and a pelvis in the course of hip surgery in order to be able to make correct securement of prosthetic hip components. Elongated first and second orientation rods are releasably securable respectively to a femur head and a hip pelvis. A gauge rod (13) extends between the two orientation rods and is displaceable along one of the orientation rods. The gauge rod is releasably securable in any of a plurality of adjusted positions longitudinally of that one orientation rod, in order to control the mutual parallelism and the distance between the two orientation rods. The orientation rod other than that one orientation rod has gauge markings thereon for determining the position of the gauge rod along that other orientation rod.

2 Claims, 6 Drawing Sheets

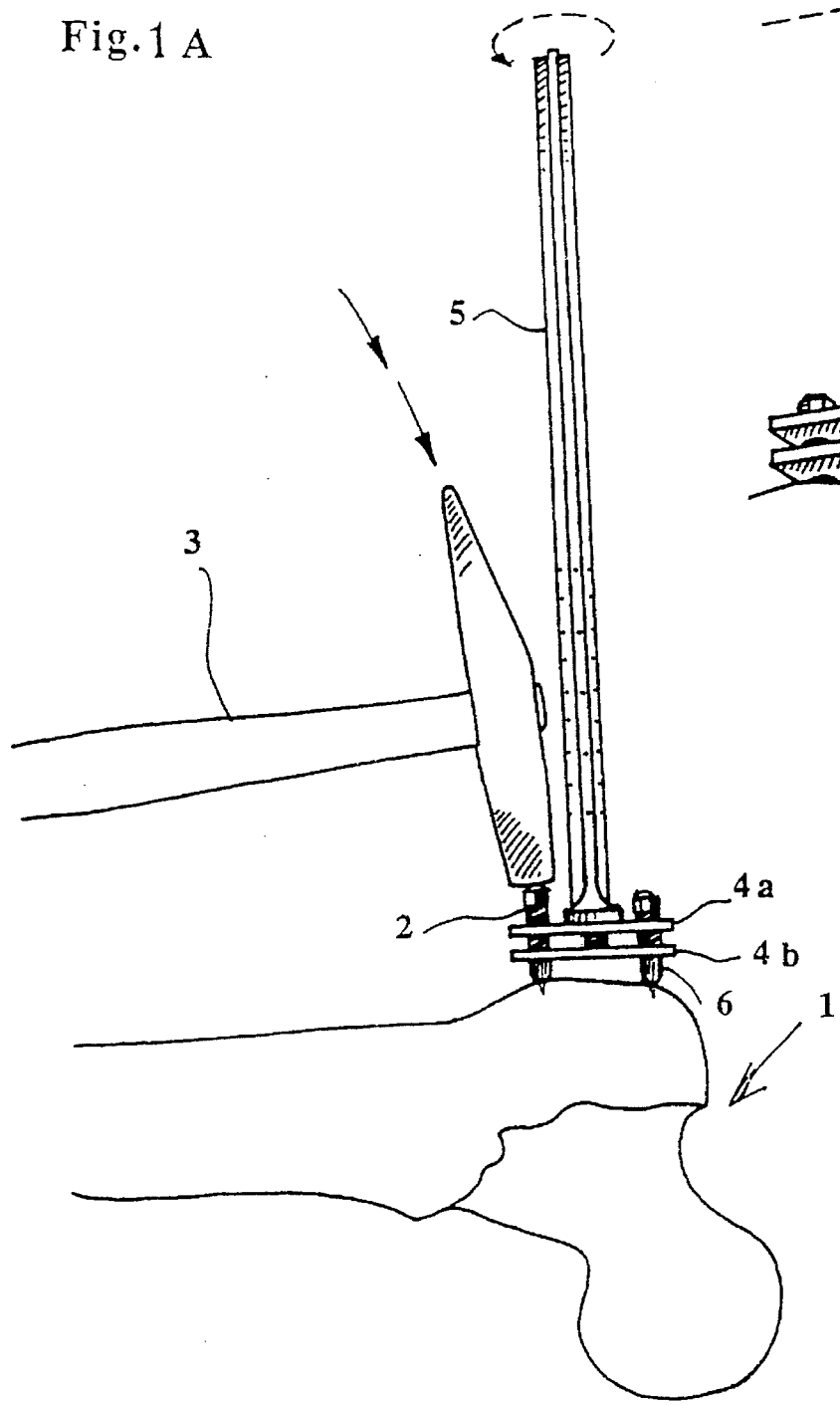
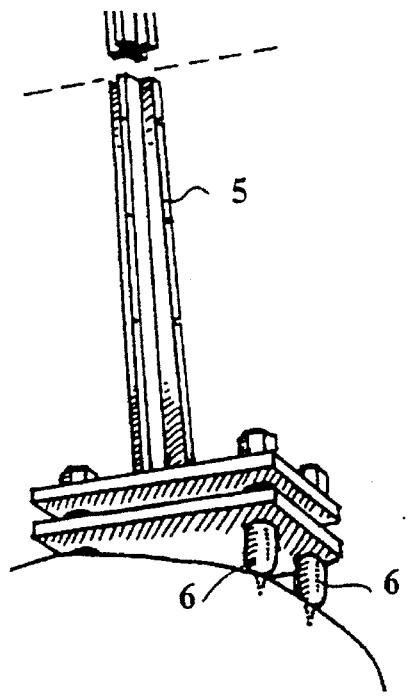
Fig. 1A
Fig. 1B

Fig. 5A
Fig. 5B
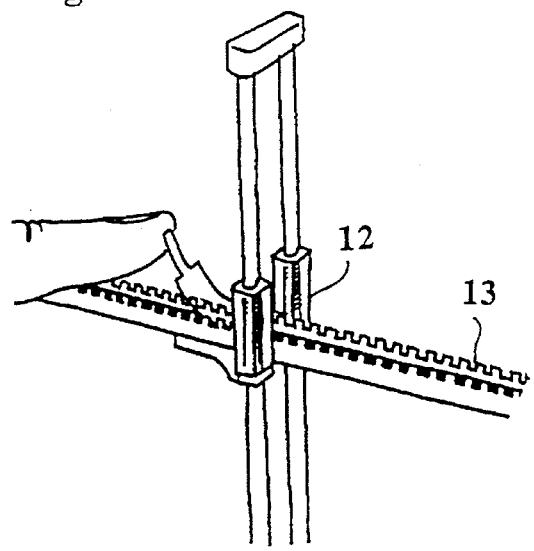
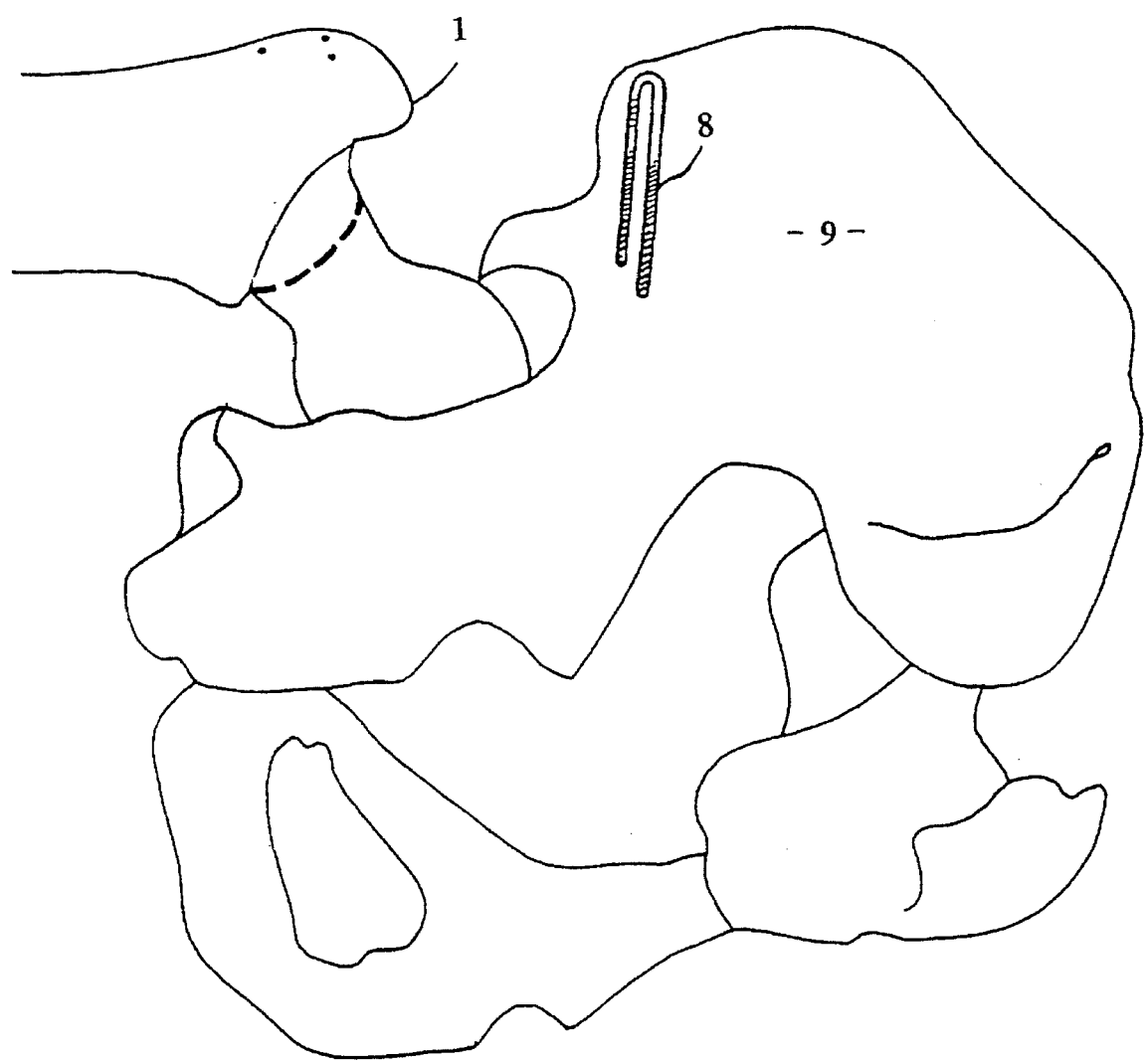

MEANS TO SAFELY DETERMINE THE MUTUAL POSITIONS OF A FEMUR AND AN ILIUM IN HIP SURGERY

The present invention relates to means to safely determine the mutual positions of a femur and an ilium in hip surgery to be able to correctly make a surgical replacement of pathologic components.

More exactly the invention relates to means for hip joint surgery giving a very high grade of certainty in obtaining a correct length of the leg, the right off-set regarding ithium and the correct joint hook of the prosthesis.

In hip joint surgery it is of vital importance to have the surgical replacement components fixed in mutual positions corresponding to the original positions of the joint components (femur head of the femur and the acetabulum of the ilium) provided that an adjustment of the length of the leg and/or the joint hook is not to be made in connection to the surgery. Thus the surgically replaced prothesis of the femur head must have essentially the same extension in the length direction in a determined angular setting to the extension of the femur as was the case for the original femur heads, and at the same time as the position of the acetabulum of the hip must allow a correct bending action in a normal position of the pelvis. The femur and the new prothesical femur head and the acetabulum in the hip are exposed to stress cycles (pressure and bending stresses) which, if concentrated on some components of the natural bone, may involve a risk of destruction of the bone. In a total hip replacement it is also important that a correct length of the leg and a correct off-set are obtained to avoid a defective walking which easily can inflict damages on other joints and muscle attachments, especially in the back of the body. Thus it is of vital importance that concentrations of stresses are evenly distributed as possible and that the position of the body after the surgery not have to be changed to compensate for incorrectly implanted prothesis components. This even distribution of stresses and the original way of moving and walking after an operation is facilitated if the implanted prothesis components will take positions that essentially correspond to the original and correctly acting, but pathologic hip.

Since hip surgery is likely and most often done to elderly people it is important that learnt and automated movement patterns of the legs can be kept unchanged as far as possible after surgery. It is well known that it is very difficult and sometimes impossible for elderly people to change a moving, pattern once learnt.

The object of the present invention is to obtain a technique making it possible to attach joint protheses in exact positions to avoid stress concentrations and destruction of the bone and to make it easier for the patient to walk again without having to adapt his/hers walking an incorrectly implanted hip joint prothesis.

The invention will now be described in connection with the drawings showing one embodiment by way of example, where FIG. 1A is a side view of a femur head in an initial position and onto which first orientation means is attached;

FIG. 1B is an enlarged view from below of a part of the first orientation means showing a possibility for adjustment;

FIG. 5A shows the femur head and pelvis after removal of the orientation means and just before the replacement of worn joint components;

FIG. 5B shows how a necessary adjustment of the length of the leg can be made prior to removal of the orientation means.

Figure 2:
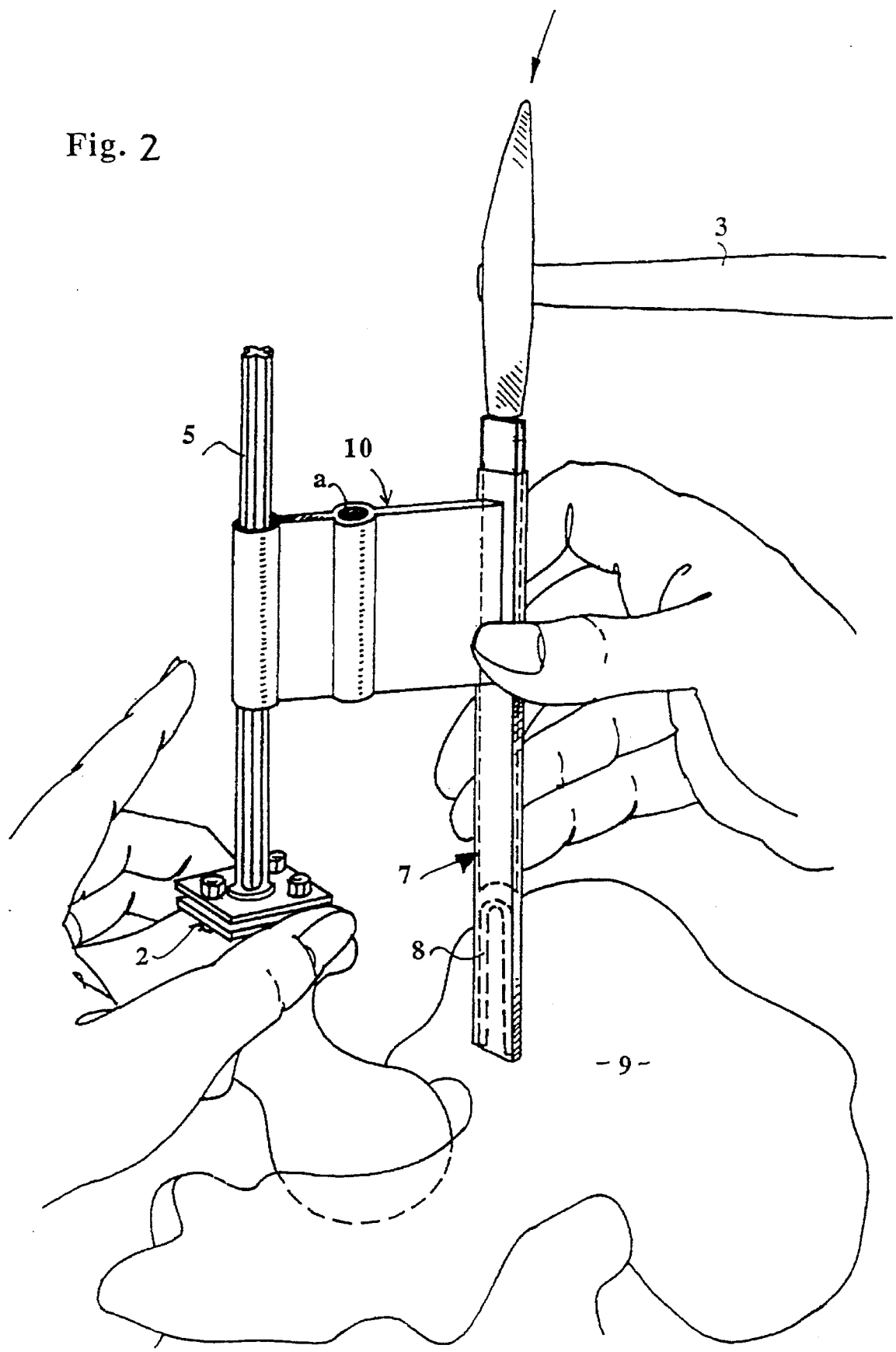
FIG. 2 is a diagrammatic view of an attachment of the other attachment means onto the pelvis.

FIG. 1A shows a femur head 1 on a trochanter surface of which a fixing means 2 in the form of a tipped screw just has been struck into the bone with a hammer 3. The screw is in threaded engagement with threaded openings in a couple of plates 4a and 4b. A first orientation means 5 in form of a measure graded sight pin (trochanter pin) is in threaded engagement with a threaded hole in the first plate 4a. The tip of the sight pin rests against a second plate, wherein a turning of the sight pin is used to mutually move the plates 4a, 4b and in this way lock the screw 2—and adjusting screw 6—after setting, the orientation means 5 and after performing an adjustment to parallelism between means 5 and 11. The tips of the adjustment screws 6 are also punched down into the trochanter surface. Thus when the sight pin is turned clock-wise both the fixing means 2 and the adjustment screws 6 are locked in their positions and if by then the means 5 and 11 are parallel a reading of the mutual positions of the hip joint components can occur.

In FIG. 1B the sight pin 5 with adjustment screws 6 making an angular adjustment of said pin possible is shown.—See further below.

In FIG. 2 holding means 7 is shown. This means is used for fixing another fixing means into the pelvis 9 in parallelism with said first fixing means 2, the holding means having distance means 10 with two openings, one of which is shown carrying the orientation means 5 (sight pin), while the other opening a is intended to be used in cases where the existing distance between the attachment positions of the fixing means 2 and 8 is shorter. Thus the opening is threaded onto the sight pin, the holding means automatically ought to be directed in parallelism with the pin 5 to safely obtain a correct position for attaching the fixing means 8 into the pelvis. This attachment takes place by pressing the sight pin 5 with the plates 4 firmly against the femur at the same time as the fixing means 8 within the holding means 7 is punched through the cortical bone, through the spongious bone down to the cortical bone where the tips of the fixing means (in this case a U-cramp) are attached.

Figure 3:
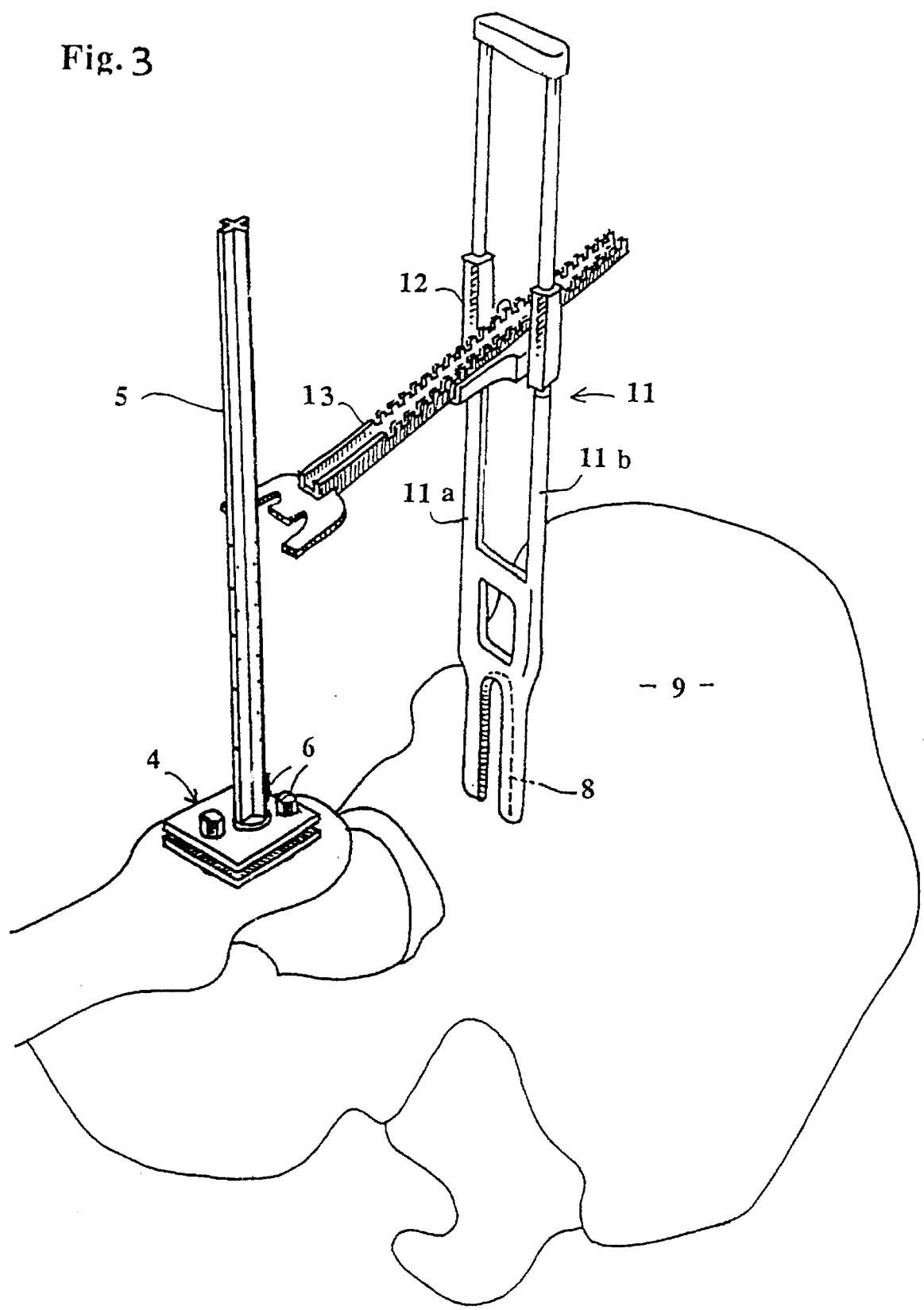
FIG. 3 shows the other orientation means being attached at the pelvis and the control of the mutual parallelism of the orientation means.

FIG. 3 is a diagrammatic view showing the arrangements of the other orientation means 11 at the pelvis 9. The orientation means 11 with two parallel stick means 11a, 11b carry adjustable yoke means 12 having a gauge rod 13. The orientation means is pressed firmly down onto the U-cramp. Thereafter the yoke means 12 is brought up and down along the stick means 11a, 11b for controlling the mutual parallelism between the orientation means 5 and 11. This parallelism is easy to read in that the end of the gauge rod 13 directed towards the orientation means 5 has a clamp-like termination, which means that the means 5 shall be situated "at the same position" within the clamp when parallel. If the parallelism doesn't exist the sight pin is turned about half a turn e.g. counterclockwise and the parallelism is set with assistance from the two set screws 6 of the plate 4 (see also FIG. 1B). Then the pin 5 is tightened clockwise for locking.

Figure 4:
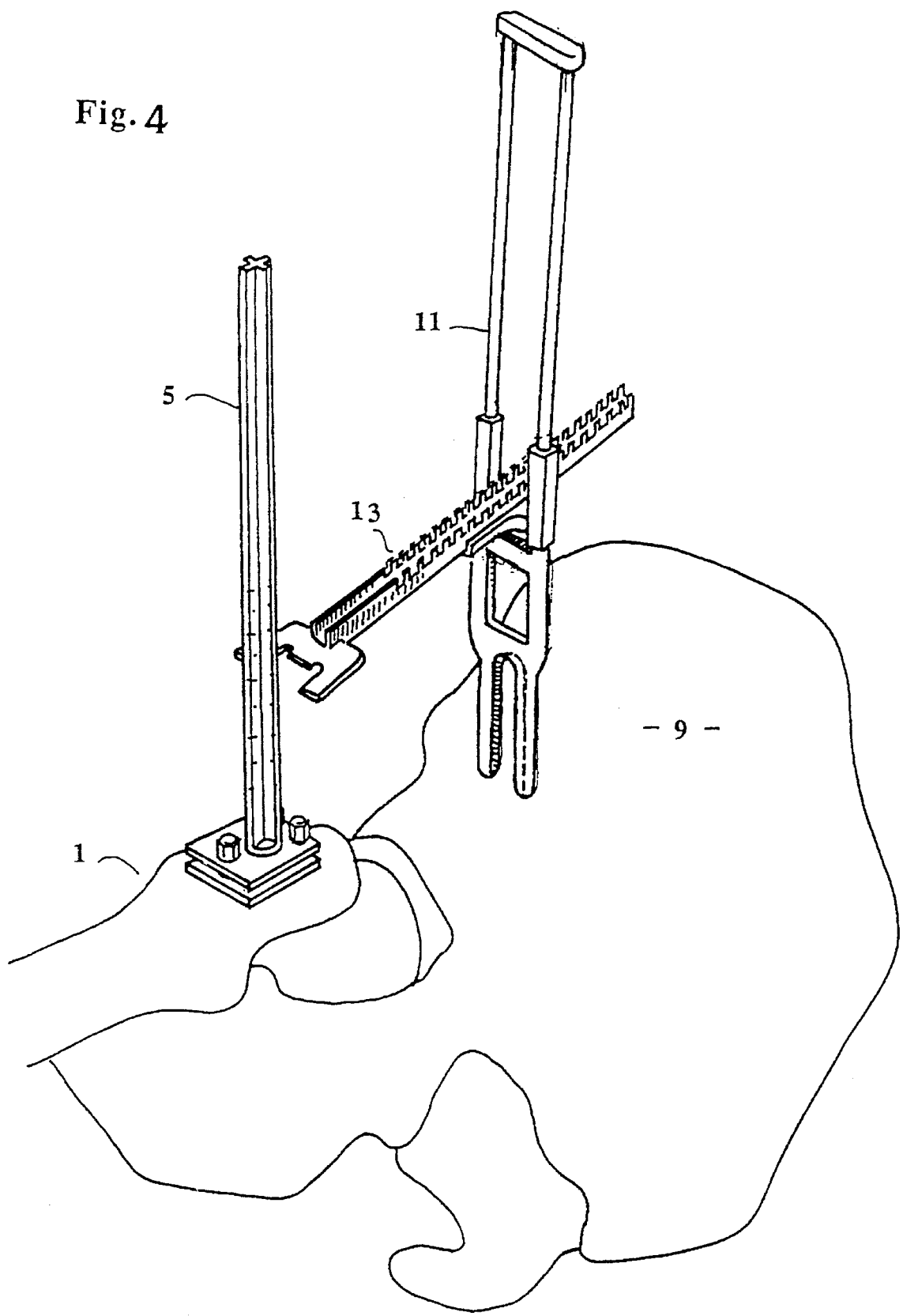
FIG. 4 shows the position for determine the distance between the two orientation means.

In FIG. 4 an initial position prior to off-set reading is shown, and from which position the yoke means is moved down to a stop (its bottom position) on the parallel rod. A reading is performed and the figures on the gauge rod of the sight pin 5 are recorded.

In FIG. 5A a femur head 1 and a pelvis 9 are shown prior to the removal of the pathologic components. Please note that an adjustment of the length now can be performed by adjusting the position of the measuring sticks within the yoke means 12.—See FIG. 5B. The fixing means 8 is left in place and the attachment holes for the plates are there for a later use to be explained below.

Figure 6:
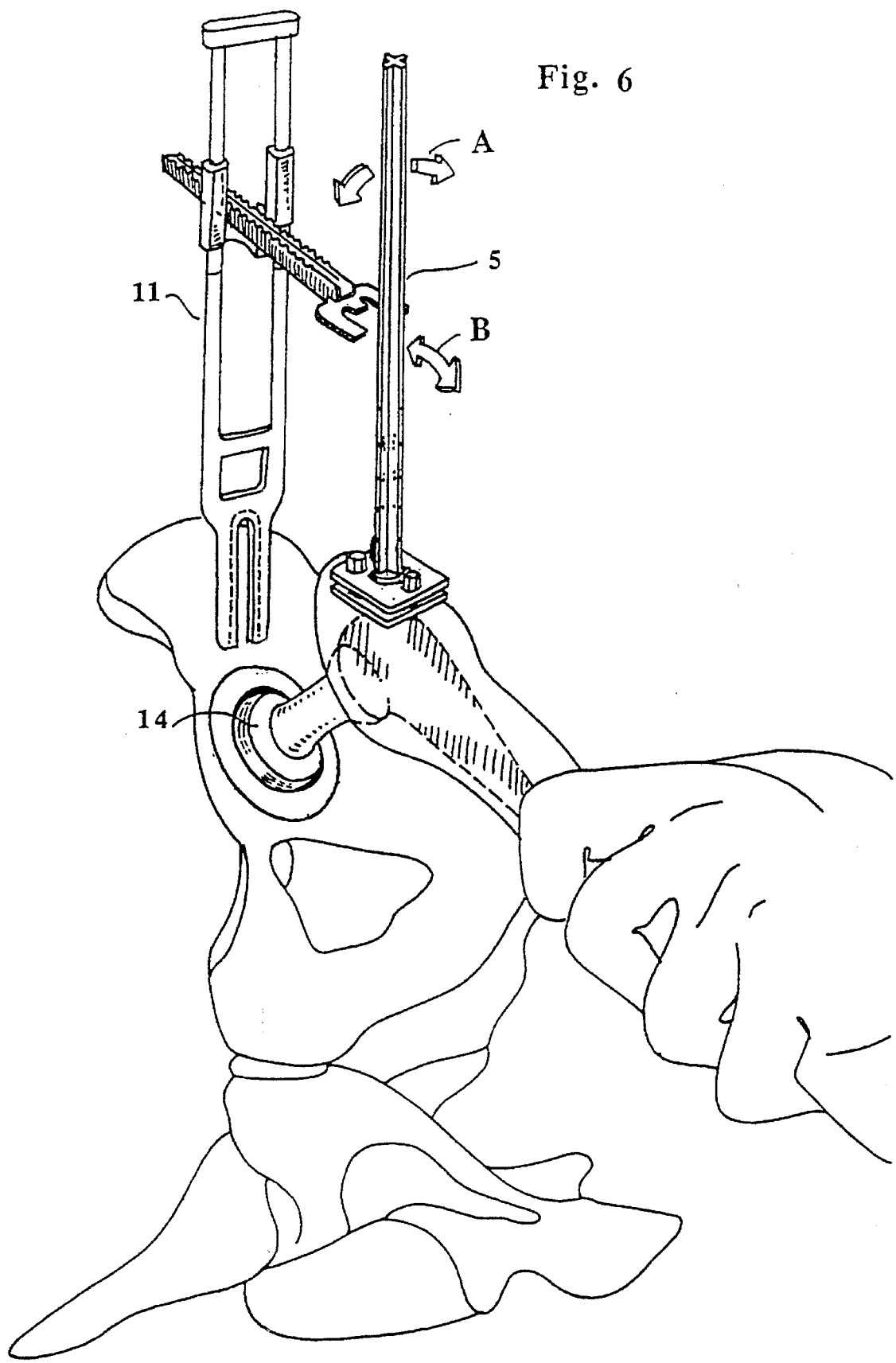
FIG. 6 shows the final adjustment of the femur and pelvis back to their initial positions prior to the final locking of the femur prosthesis components.

In FIG. 6 is shown how the orientation means 5 and 11 have been replaced onto their fixing means in the required positions, which means that each of the orientation means 5 and 11 will take their initial positions (in regard to the femur head and the pelvis, respectively) they had when the distance between them was decided, as long as an adjustment of the length did not take place. (FIG. 5B). In practice this it is done according to the following. When the acetabulum is fixed in the pelvis, but the femur head prothesis is not cemented, the orientation means with gauge rod are once again attached in place with the screws being properly pressed down into the attachment or orientation holes already made in the trochanter surface of the femur head. After that the femur is moved so that the sight pin 5 is moving in the planes of the arrows A and B until the pin is parallel with the orientation means 11. In this position it is possible to see if the length and the off-set is correct. If the positions do not agree an adjustment of the prothesis component 14 takes place until parallelism is obtained. Thereafter the component 14 is fixed too.

The invention not limited to the embodiment above, but modifications can be done within the scoop of the appended claims.

I claim:

1. Apparatus to determine the mutual positions of a femur head and a pelvis in the course of hip surgery in order to be able to make correct securement of prosthetic hip components, comprising elongated first and second orientation means, means for releasably securing each of said first and second elongated orientation means respectively to a femur head and to a hip pelvis, a gauge rod (13) extending between the two orientation means, means mounting the gauge rod for displacement along one of the orientation means, and means for releasably securing the gauge rod in any of a plurality of adjusted positions longitudinally of said one orientation means, in order to control the mutual parallelism and the distance between the two orientation means.

2. Apparatus according to claim 1, wherein the orientation means other than said one orientation means has gauge markings thereon for determining the position of the gauge rod along said other orientation means.

* * * * *